United States Patent [19]

Mullin et al.

[11] Patent Number: 5,289,255
[45] Date of Patent: Feb. 22, 1994

[54] CUVETTE FOR USE IN MAKING A MEASUREMENT OF A BLOOD PARAMETER AND ASSEMBLY UTILIZING THE SAME

[75] Inventors: Paul J. Mullin, Westminster; Stan O. Heinemann, Trabuco Canyon; Mark G. Gordon, Tustin, all of Calif.

[73] Assignee: Minnesota Mining and Manufacturing Co., St. Paul, Minn.

[21] Appl. No.: 676,956

[22] Filed: Mar. 28, 1991

[51] Int. Cl.⁵ .................. G01N 1/10; G01N 33/48
[52] U.S. Cl. .................. 356/246; 356/41
[58] Field of Search .............. 356/39, 40, 41, 244, 356/246, 410, 411; 128/633, 664; 250/339; 307/116, 113, 149; 335/206, 207; 422/102, 104, 44, 45; 235/375, 449, 493

[56] References Cited

U.S. PATENT DOCUMENTS

| | | | |
|---|---|---|---|
| 2,912,540 | 11/1959 | Sawicki | . |
| 3,581,030 | 5/1971 | Sedley | 335/206 |
| 4,210,889 | 7/1980 | Holce | 335/207 |
| 4,227,810 | 10/1980 | Sandrock et al. | 356/246 |
| 4,301,804 | 11/1981 | Thompson et al. | 128/419 PG |
| 4,331,013 | 5/1982 | Jaulmes | 335/206 |
| 4,349,814 | 9/1982 | Akehurst | 307/116 |
| 4,444,498 | 4/1984 | Heinemann | 356/246 |
| 4,447,150 | 5/1984 | Heinemann | 356/409 |
| 4,580,062 | 4/1986 | MacLaughlin | 307/116 |
| 4,631,693 | 12/1986 | Neri | 364/550 |
| 4,640,820 | 2/1987 | Cooper | 422/68 |
| 4,728,928 | 3/1988 | Shipley | 335/205 |
| 4,729,661 | 3/1988 | Bell | 356/246 |
| 4,745,279 | 5/1988 | Karkar et al. | 356/40 |
| 4,765,345 | 8/1988 | Adib | 128/777 |
| 4,812,674 | 3/1989 | Sue et al. | 307/116 |
| 4,856,339 | 8/1989 | Williams | 73/714 |
| 5,046,496 | 9/1991 | Betts et al. | . |
| 5,066,859 | 11/1991 | Karkar et al. | 250/339 |
| 5,104,623 | 4/1992 | Miller | 422/82.06 |

FOREIGN PATENT DOCUMENTS 2618233 11/1977 Fed. Rep. of Germany .
1453602 10/1976 United Kingdom .

Primary Examiner—Richard A. Rosenberger
Assistant Examiner—Hoa Q. Pham
Attorney, Agent, or Firm—Gordon L. Peterson

[57] ABSTRACT

A cuvette comprising a housing having a passage therethrough and being adapted to receive blood. The housing has a wall with an outer face. An optical window leads from the outer face to the passage and the optical window is transmissive to an optical signal so that a parameter of blood in the passage can be measured. A magnet is carried by the wall and spaced from the optical window for use in providing information about the cuvette. The cuvette is releasably attachable to an optical head. The optical head includes a plurality of Hall effect transducers which respond to the position of the magnet on the housing so that the position of the magnet can be used to provide information about the cuvette.

17 Claims, 3 Drawing Sheets

CUVETTE FOR USE IN MAKING A MEASUREMENT OF A BLOOD PARAMETER AND ASSEMBLY UTILIZING THE SAME

BACKGROUND OF THE INVENTION

It is often necessary or desirable to measure various blood parameters, such as blood gases, pH, hematocrit, oxygen saturation, etc. This can be accomplished in real time by passing blood through a cuvette and directing one or more appropriate optical signals through an optical window toward the blood in the cuvette. An optical signal is provided by the blood parameter of interest which can be used to measure this blood parameter in accordance with known techniques. Specific examples of a cuvette for measuring blood oxygen saturation and hematocrit are shown in Heinemann U.S. Pat. No. 4,444,498 and Karkar et al U.S. Pat. No. 4,745,279, respectively.

In the case of measuring hematocrit or blood oxygen saturation, the cuvette is coupled to an instrument which provides light at appropriate wavelengths for directing through the optical window and into the blood in the passage of the cuvette. The blood returns a portion of this light in the form of an optical signal back to the instrument where it is appropriately processed to determine hematocrit and/or oxygen saturation.

In order that accurate data is obtained, it is essential that the cuvette be properly optically coupled to the instrument. Without proper optical coupling, there may be a loss of optical signal which would yield an inaccurate measurement of hematocrit or oxygen saturation. For example, the cuvette may be nearly, but not completely, coupled to the instrument in such a way that it would appear to the attendant that proper coupling was achieved. This, however, would provide inaccurate measurements due to signal loss and/or admission of ambient light into the signal path.

Another factor which, by way of example, might provide for a degradation in accuracy results from the use of unauthorized cuvettes. An unauthorized cuvette may not properly mate with the instrument or optical head or its optical path may have different characteristics that may introduce error into the calculations.

It would also be desirable to be able to automatically provide information about the cuvette to the instrument. Although this could be provided manually by an attendant, doing so automatically eliminates the possibility of attendant error. One example of this would be to provide information to the instrument as to the diameter or cross-sectional area of the passage through the cuvette so that the instrument would know, for example, if the cuvette were ⅛ or ¼ inch in diameter. With this information, the instrument could then utilize the appropriate algorithm and/or terms in an algorithm to properly calculate hematocrit and/or blood oxygen saturation.

SUMMARY OF THE INVENTION

This invention solves these problems while providing a number of other features and advantages. With this invention, a magnet is used to provide various information about the cuvette. For example, this information may include whether or not the cuvette is properly optically coupled into the system, whether or not the cuvette is an authorized cuvette and/or other factors of interest, such as the diameter or cross-sectional area of the passage in the cuvette.

The magnet can be used in various different ways to achieve these very desirable results. For example, if the cuvette is to be optically coupled to an optical head, a Hall effect transducer in the optical head may be actuated by the magnet to thereby indicate that a proper optical and mechanical connection has been made between the cuvette and the optical head and that the cuvette is an authorized cuvette. The Hall effect transducer is only actuated if proper coupling between the cuvette and optical head is achieved because if this is not achieved, the magnet will be too remote from the Hall effect transducer to actuate it.

If it is desired to provide additional information concerning the cuvette, such as the diameter of the passage in the cuvette, the optical head includes more than one Hall effect transducer. In this event, when the cuvette is properly coupled to the optical head, the magnet will be sufficiently close to one of the Hall effect transducers to actuate it and sufficiently far from the other of the Hall effect transducers so that they remain unactuated. Thus, the position of the magnet, and hence which of the Hall effect transducers is actuated, is used to provide additional information to the instrument.

For example, with three Hall effect transducers and one magnet, three different items of information can be provided in addition to confirmation of proper coupling and authorization of the cuvette. Although more information of this type could be transmitted by employing additional magnets, if additional information needs to be transmitted, it is preferred to add additional transducers to the optical head. This is less expensive than adding magnets because the magnets are in the cuvette, which is a disposable item and the optical head is reusable. Accordingly, the preferred construction uses only a single magnet.

A cuvette which embodies this invention and is usable in making a measurement of a blood parameter includes a housing having a passage with the passage having a biocompatible surface and being adapted to receive blood. The housing also has a wall with an outer face. An optical window leads from the outer face to the passage, and the optical window is transmissive to an optical signal so that the parameter of the blood can be measured. The magnet is between an outer face of the optical head and the passage of the housing and is preferably carried by the wall and spaced from the optical window. Preferably, the passage is a flow-through passage which extends entirely through the cuvette.

To facilitate assembly and to insure that the magnet is correctly positioned, the wall preferably has a recess opening at the outer surface, and the magnet is retained in the recess. Preferably the wall contains a plurality of recesses, any one of which is sized to receive and retain the magnet. If the cuvette is a molded part, then only a single mold is required regardless of where the magnet is located.

The housing is releasably couplable to the optical head. To accomplish this, the housing has first and second coupling members, and the orientation of the optical window and magnet in relation to these coupling members, while not absolutely essential, is important and can be used to provide noteworthy advantages. For example, to provide good optical coupling and good magnetic coupling between the magnet and the transducer of the optical head, the magnet and optical window are preferably between the coupling members.

In a preferred arrangement, the first coupling member is useful in pivoting the housing to the optical head and the optical window is between the first coupling member and the magnet. With this arrangement, the magnet is located farther from the pivot axis where it is more sensitive to any angular deviation which would suggest an improper mechanical connection.

To provide improved optical coupling, the optical window preferably includes a region of the outer wall and a deformable optical coupling element on the outer face at such region of the outer wall. The deformable optical coupling element can be squeezed between such region of the wall and a confronting wall of the optical head to exclude moisture from the optical path and to provide a repeatable optical coupling.

One other advantage of the pivotal connection between the cuvette and the optical head is that the pivot action tends to squeegee away any air or moisture on the outer surface of the deformable optical coupling element to provide improved optical coupling. This squeegee action occurs automatically because of the pivotal connection between the cuvette and the optical head. The squeegee action is enhanced by placing the deformable optical coupling element nearer to the first coupling member, which is the coupling member that is used to provide the pivot connection, than to the second coupling element.

Although the coupling members can take different forms, in one preferred form, the first coupling member has a recess which is capable of receiving a projection on the optical head to enable the pivotal motion to occur. The second coupling member is useful in retaining the cuvette and optical head in the closed position in which their respective outer faces are in confronting relationship. This may be accomplished, for example, by a coupling member which has a ledge spaced from, and facing, the outer face of the cuvette.

In a preferred construction, the passage and the housing are both elongated and the magnet and optical window are spaced longitudinally. The optical window is preferably oriented so that an axial reference plane extending through a longitudinal axis of the passage bisects the optical window. This orientation minimizes unwanted reflection. However, the magnet preferably lies on one side of said plane. To assist in making a better optical coupling, the outer face of the cuvette is preferably generally flat, and it is elongated. The coupling members are preferably located adjacent the opposite ends of the outer face.

To assure that the passage through the cuvette is adapted to receive blood, it is preferably sterile and constructed of a biocompatible material. A molded plastic, such as polycarbonate, is preferred.

The invention, together with additional features and advantages thereof may best be understood by reference to the following description taken in connection with the accompanying illustrative drawings.

DESCRIPTION OF THE PREFERRED EMBODIMENT

Figure 1:
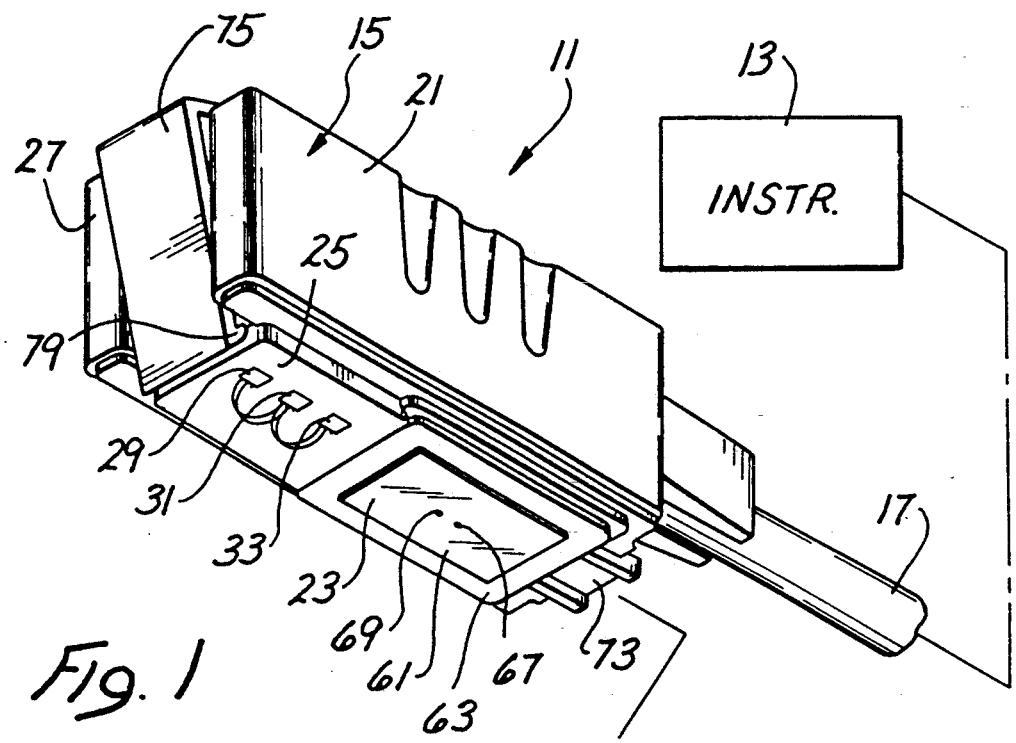
FIG. 1 is a partially schematic perspective view illustrating an assembly constructed in accordance with the teachings of this invention.
Figure 2:
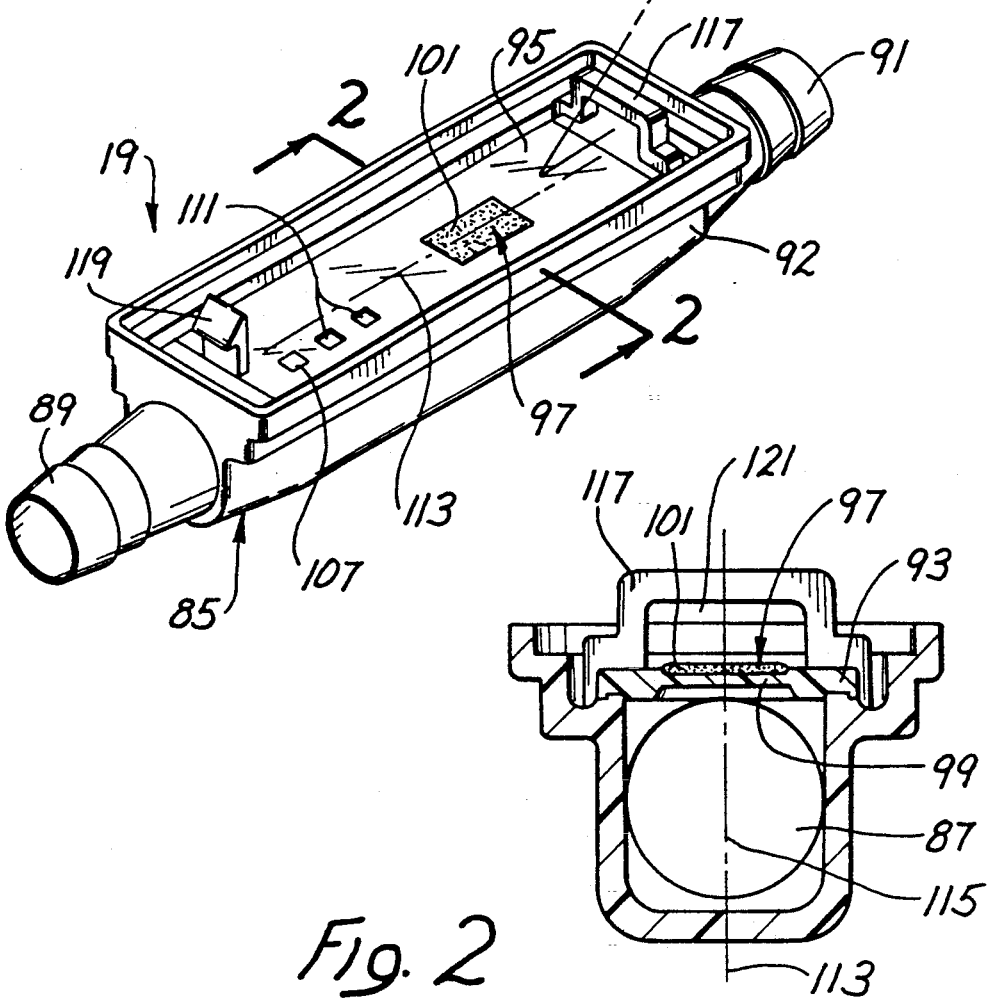
FIG. 2 is a sectional view taken generally along line 2—2 of FIG. 1.

FIG. 1 shows an assembly which comprises an instrument 13, an optical head 15, electrical and optical conductors 17 for coupling the optical head to the instrument and a cuvette 19. The assembly 11 is of the type which measures hematocrit and blood oxygen saturation and may accomplish this utilizing the techniques disclosed in common assignees co-pending application Ser. No. 652,121 filed on Feb. 7, 1991, naming Stan O. Heinemann, Paul J. Mullin and Susan Cavanaugh as the inventors and entitled APPARATUS AND METHOD FOR MEASURING A BLOOD PARAMETER.

The optical head 15 includes a body 21 having an outer face 23. The body 21 forms, in effect, a housing and supporting structure for the optical head 15 and includes a base 25 and a shell 27 with the base 25 closing the lower (as viewed in FIGS. 1 and 4) end of the shell. The base 25 is suitably coupled to the shell 27 as by fasteners (not shown). Hall effect transducers 29, 31 and 33 are mounted in a row in longitudinally spaced relationship on a rear face of the base 25.

The base 25 has an opening 37 (FIG. 4) which receives an elastomeric gasket 39 which is held in place by a gasket retainer 41 adhered to the base 25 and by a projection 43 on the base. A circuit board 45 is retained within and is surrounded by the gasket 39 between a ledge 47 and a circumscribing projection 49 of the gasket 39. A metal carrier 50 has pins 51 which project through the circuit board 45. Light emitting diodes 53 and 55 which emit in the red and infrared ranges, respectively, are suitably mounted, such as on a ceramic substrate 56, inside the metal carrier 50 along with an optical detector 57 and a reference detector 59 which are also mounted on ceramic substrates 58. A metal plate 60 is suitably attached to the carrier 50 as by an epoxy, and the lower side (as viewed in FIG. 4) of the plate 60 is sealed off by a layer 61 of hard, clear epoxy and a rim 63 of the gasket 39 surrounds the layer 61 as shown best in FIG. 1. The layer 61 is transparent to light from the diodes 53 and 55 and to reflected light from the blood. A divider 65 provides optical isolation between the light emitting diodes 53 and 55 and the detector 57.

Apertures 67 and 69 in the plate 60 provide optical communication to the exterior of the optical head 15 for the diodes 53 and 55 and the detector 57, respectively. With this arrangement, if the layer 61 is loaded tightly against an external surface, the loading pressure reacts through the circuit board to the gasket 39 and onto the projection 49. This displaces the material of the gasket 39 into a circumscribing recess 71 to allow the layer 61 to move upwardly (as viewed in FIG. 4) to accommodate the surface against which it is pressed.

Figure 3:
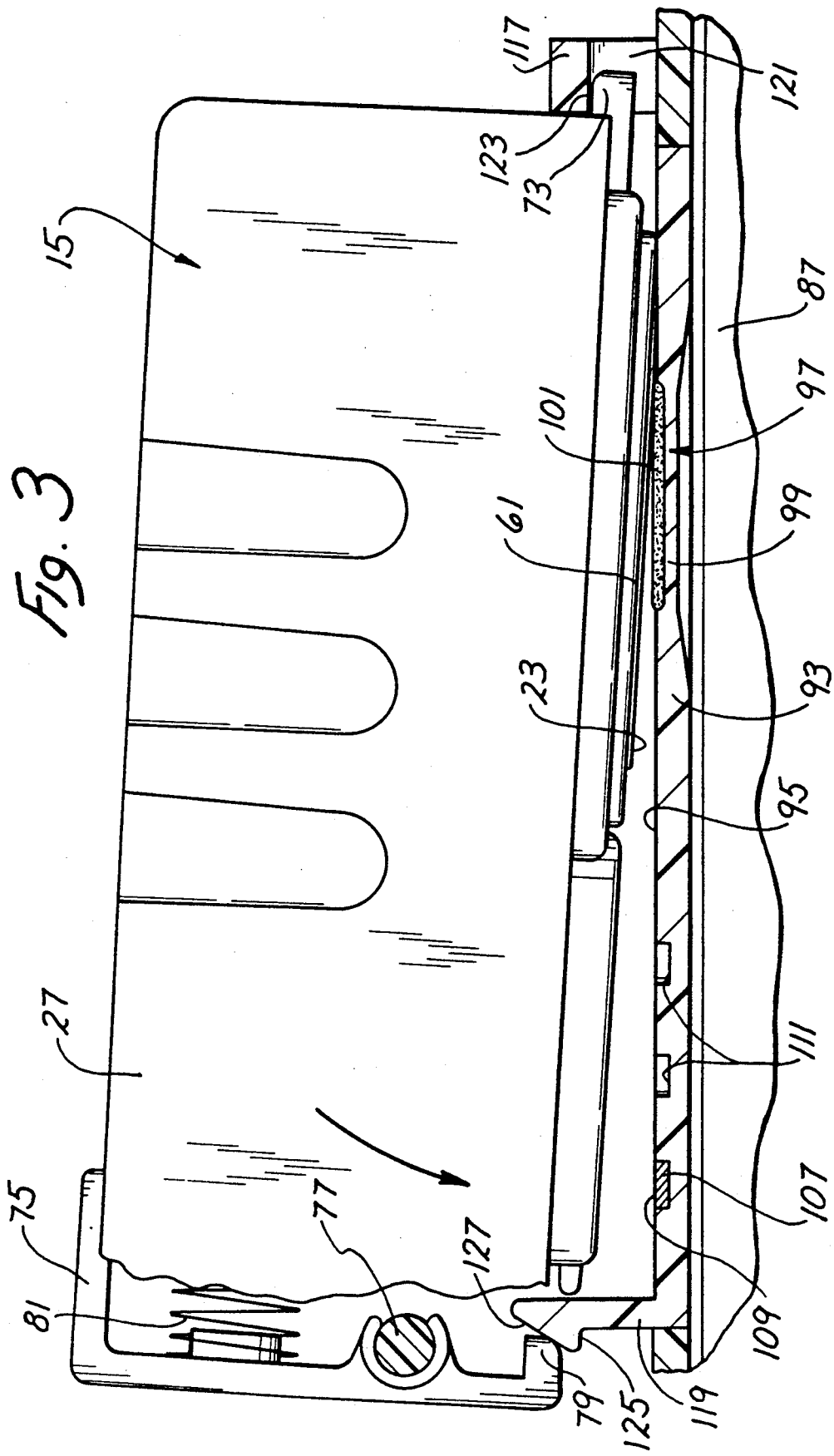
FIG. 3 is a fragmentary elevational view partially in section showing the pivoting of the optical head and cuvette.

To facilitate coupling of the optical head 15 to the cuvette 19, the optical head has a coupling member in the form of a projecting tab 73 extending outwardly from one end of the base 25 and a pivotal coupling member 75 which is pivotally attached to the shell 27 by a pin 77. The coupling member 75 terminates in a hook 79. A spring 81 normally biases the coupling member 75 counterclockwise as shown in FIG. 3.

The cuvette 19 includes a housing 85 which, in the embodiment, is integrally molded of transparent polycarbonate. The housing 85 is elongated and has an elongated, smooth, generally cylindrical passage 87 extending therethrough. The surface of the passage 87 and the entire housing 85 are constructed of a biocompatible material. The passage 87 is smooth to better accommodate blood flow therethrough. The entire cuvette 19 is sterilized to make it suitable for medical usages. The housing 85 has integral tube fittings 89 and 91 for use in coupling of the housing, and in particular the passage 87, to tubing (not shown) for conducting blood through the passage 87. For example, the cuvette 19 may be used in an extracorporal blood loop.

The housing 85 includes a main body 92 with an open upper (as viewed in FIG. 1) end and a wall 93 which is adhered to the main body 92 to close the upper end of the main body. The housing 85 has an outer face 95 which is generally flat and planar. Most of the outer surface is formed by the wall 93.

An optical window 97 is provided which leads from the outer face 95 to the passage 87. The optical window 97, in this embodiment, is transmissive to red and infrared optical signals from the diodes 53 and 55. However, the optical window 97 should be transmissive to whatever wavelengths are being employed for the particular blood parameter test of interest. The optical window 97 includes a region 99 of the outer wall and a deformable optical coupling element 101 on the outer face 95 at the region 99. As shown in FIGS. 2-5, the region 99 is thinner than an adjacent portion of the wall 93. The coupling element 101 is preferably constructed of a which has an index of refraction near the index of infraction of the wall 93.

Although various constructions are possible, the coupling element 101 in this embodiment is retained by a clear adhesive in a recess 103 of the wall 93. In the relaxed configuration, the coupling element 101 projects out of the recess 103 (FIG. 5) to better facilitate the squeegee action referred to above.

Figure 5:
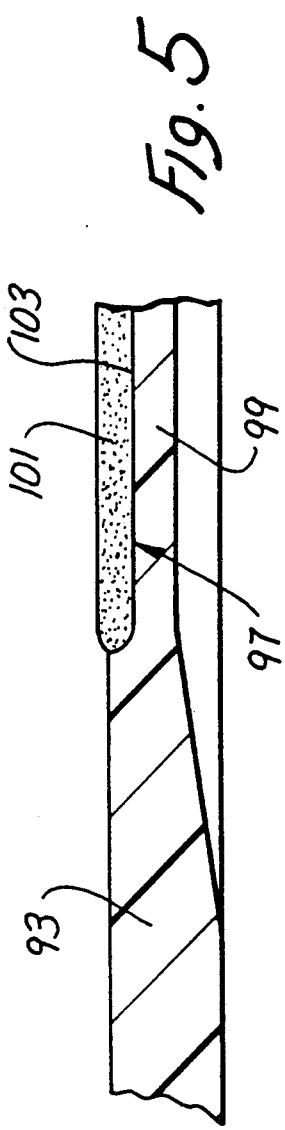
FIG. 5 is a fragmentary sectional view illustrating a portion of the wall of the cuvette containing the deformable optical coupling element.

To minimize the length of the optical path through the wall 93, the region 99 is thinned to a thicken substantially less than the thickness of the remainder of the wall 93 as shown in FIG. 5. Consequently, there is a smooth elongated channel 105 adjacent the region 99.

A magnet 107 is carried by the wall 93 in longitudinally spaced relationship to the optical window 97. In this embodiment, the magnet 107 is adhesively retained in a recess 109 which opens at the outer face 95 as shown in FIG. 3. In this embodiment, the wall 93 has two other recess 111, which are identical to the recess 109, so that during manufacture, there is a choice of three separate locations for the magnet 107. The recesses 109 and 111 are aligned in axially or longitudinally spaced relationship, and they form a longitudinally extending or axially extending row.

With respect to orientation, the optical window is located so that an axial reference plane 113 (FIG. 2) extending through a longitudinal axis 115 of the passage 87 bisects the optical window. By so doing, unwanted reflections from the surface of the passage 87 are minimized. The magnet 107 and all of the recesses 109 and 111 lie on one side of the reference plane 113 as shown in FIG. 1.

To releasably couple the cuvette 19 to the optical head 15, coupling members 117 and 119 are provided on the housing, and more specifically adjacent the opposite longitudinal ends of the outer face 95. The coupling member 117 is useful in pivoting the cuvette 19 to the optical head 15. More specifically, the coupling member 117 defines a recess 121, which in this embodiment is an opening, for receiving the tab 73 as shown in FIG. 3 to form a pivotal connection for pivoting the optical head 15 generally about a pivot axis 123 (FIG. 3) which extends transverse to the longitudinal axis 115 and to the reference plane 113.

The coupling member 117 may be formed integrally with the housing 85 or it may be formed separately and attached to the outer face 95. The coupling member 119 is preferably molded integrally with the wall 93 and, like the coupling element 117, projects upwardly from the outer face 95 generally perpendicular to the outer face. The coupling member 119 has a ledge 125 spaced from and facing the outer face 95 as shown in FIG. 3. The coupling member 119 also has an inclined cam surface 127 for cooperating with the coupling member 75 of the optical head 15 as shown in FIG. 3. The coupling members 119 and 75 cooperate to retain the outer face 23 of the optical head 15 in confronting relationship with the outer face 95 of the cuvette 19. Thus, the coupling members 75 and 117 serve as a pivotal connection to pivotally couple the optical head 15 to the cuvette 19 for pivotal movement about the pivot axis 123 between a separated position as shown for example in FIG. 3 in which the outer faces 95 and 23 are essentially out of engagement and a closed or confronting position in which the outer faces 95 and 23 are in confronting relationship and in engagement. The coupling members 75 and 119 cooperate to serve as a retainer to releasably lock the optical head 15 and the cuvette 19 in the closed or confronting position by virtue of the hook 79 engaging the ledge 125 as shown in FIG. 4.

The optical window 97 and the magnet 107 are between the coupling elements 117 and 119. More specifically, the optical window 97 is closer to the coupling element 117 than the coupling element 119, and conversely, the magnet 107 is closer to the coupling element 119 than to the coupling element 117. The magnet 107 is fairly closely adjacent the coupling member 119 in this embodiment, and the optical window 97 is between the magnet and the coupling member 117.

Figure 4:
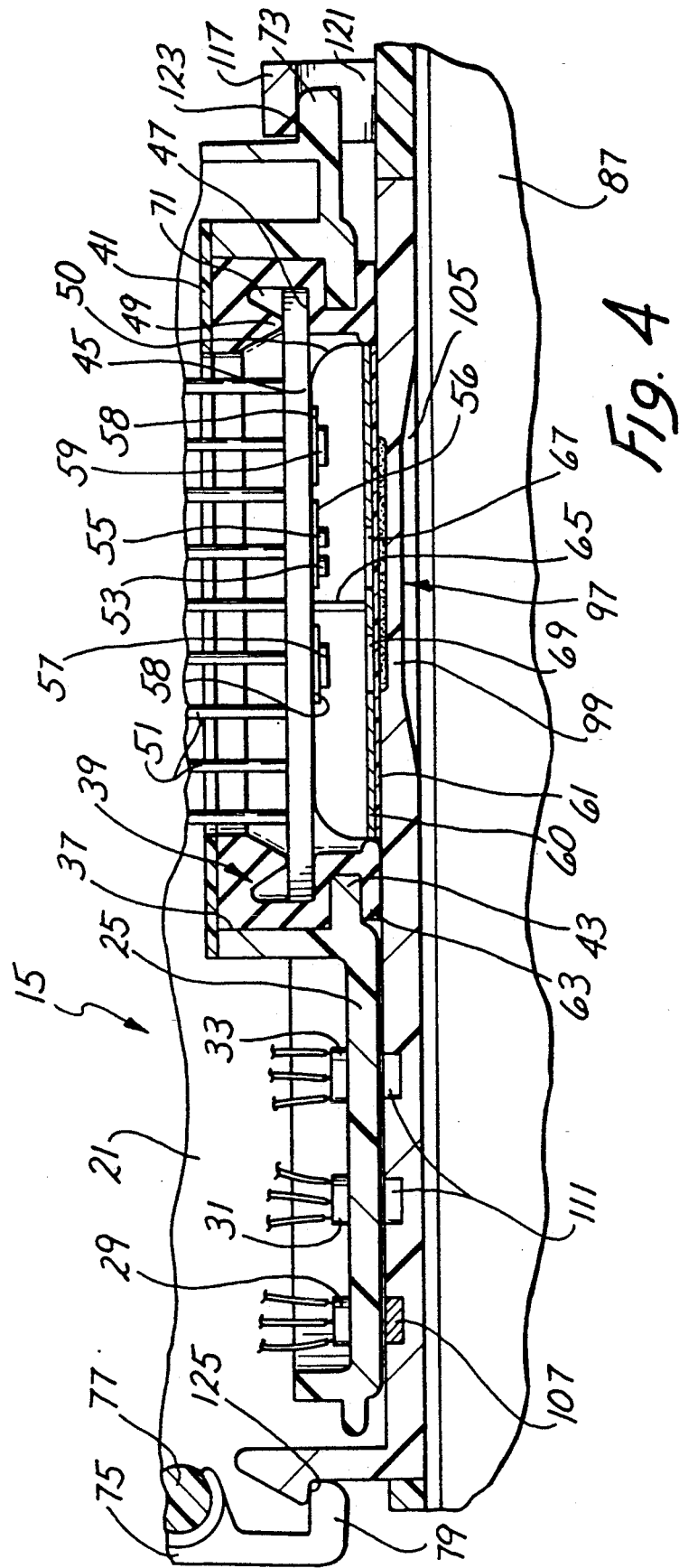
FIG. 4 is a fragmentary axial sectional view through the assembled cuvette and optical head.

In use, the optical head 15 and cuvette 19 are pivoted about the axis 123 toward the closed position of FIG. 4, and in so doing the outer face 23, and in particular the layer 61 is caused to progressively squeeze the protruding portion of the deformable optical coupling element 101 to, in effect, squeegee any air and moisture off these confronting surfaces and toward the left as viewed in FIG. 3. This squeezing action is enhanced by the fact that the deformable coupling element 101 is relatively close to the pivot axis 123.

When the closed position of FIG. 4 is reached, the layer 61 is loaded tightly against the deformable optical coupling element 101 so that a moisture free, repeatable optical coupling is provided between the diodes 53 and 55 and the passage 87 and between the passage 87 and the detector 57. The reference detector 59 receives only light from the diodes 53 and 55 which has been reflected light off of the plate 60. In addition, the magnet 107 directly confronts the Hall effect transducer 29 so that the magnetic field from the magnet 107 can actuate the Hall effect transducer 29 if the hook 79 is latched beneath the ledge 125, i.e. if the cuvette 19 is properly coupled to the optical head 15. The sensitivities of the transducers 29, 31 and 33 are such that without proper coupling, none of them is actuated. The actuation of the transducer 29 provides a signal to the instrument 13 confirming that proper optical and mechanical coupling between the optical head 15 and the cuvette 19 has been attained. In addition, because an unauthorized cuvette would not be expected to have any magnet, or a magnet that would actuate only the transducer 29, this signal also indicates that the cuvette 19 is an authorized cuvette for use with this system.

With the optical head properly coupled to the cuvette 19, the magnet 107 is sufficiently far from the transducers 31 and 33 so that these transducers remain unactuated. Accordingly, if more than one of the transducers 29, 31 and 33 is actuated, as by placing a magnet across two or more of the transducers, this change of state on the part of more than one of the transducers would indicate that the cuvette is not an authorized cuvette and the instrument would not operate. Accordingly, a proper signal to indicate both proper coupling and an authorized cuvette is a signal from only one of the transducers 29, 31 and 33.

In addition, the position of the magnet 107 on the housing 85, or more specifically in the recesses 109 and 111, can be used provide other information about the cuvette 19. With proper coupling of the cuvette 19 to the head 15, a magnet in the center recess 111 actuates only the transducer 31 and a magnet in the end recess activates only the transducer 33. For example, the magnet position may be used to identify the diameter of the passage 87 as ⅜ inch, ¼ inch and ⅛ inch by placing the magnet 107 in the recess 109, the center recess 111 or the end recess 119, respectively. This signal from the appropriate transducer 29, 31 or 33 can be used by the instrument to make any necessary adjustment required for hematocrit and oxygen saturation calculations. As a further example, magnet position may be used to inform the instrument 13 about the optical properties of the optical window 97, and this is useful if different series of the cuvette have different optical properties.

The transducers 29, 31 and 33 may initially be in either state, and the actuation of the transducer by the magnet 107 changes the transducer to the other state. If desired, the transducers may be polarity sensitive. Although other kinds of magnetic switches, such as reed switches many be used in lieu of the Hall effect transducers, the latter are preferred.

Although an exemplary embodiment of the invention has been shown and described, many changes, modifications and substitutions may be made by one having ordinary skill in the art without necessarily departing from the spirit and scope of this invention.

We claim:

1. A cuvette for use in making a measurement of a blood parameter, said cuvette comprising:
   a housing having a passage therein, said passage having a biocompatible surface and being adapted to receive blood;
   said housing having a wall with an outer face;
   an optical window leading from said outer face to said passage, said optical window being transmissive to an optical signal so that the parameter of the blood can be measured;
   a magnet carried by said wall for use in providing information about the cuvette;
   the housing being elongated and the cuvette including first and second coupling members on said housing for use in releasably coupling the housing to an optical head, said optical window and said magnet being between the first and second coupling members; and
   the first coupling member being useful in pivoting the cuvette to the optical head and the optical window including a deformable optical coupling element on said outer face between the first coupling member and the magnet.

2. A cuvette for use in making a measurement of a blood parameter, said cuvette comprising:
   a housing having a passage therein, said passage having a biocompatible surface and being adapted to receive blood;
   said housing having a wall with an outer face;
   an optical window leading from said outer face to said passage, said optical window being transmissive to an optical signal so that the parameter of the blood can be measured;
   the optical window including a region of the wall and a deformable optical coupling element on said outer face at said region of said wall;
   first and second coupling members on said housing for use in releasably coupling to an optical head;
   the first coupling member being useful in pivoting the housing to the optical head; and
   the optical window being nearer to the first coupling member than to the second coupling member.

3. A cuvette as defined in claim 2 wherein the first coupling member has a recess capable of receiving a projection and the second coupling member has a ledge spaced from and facing the outer face.

4. A cuvette as defined in claim 2 wherein the outer face is generally flat and elongated and the first and second coupling members are adjacent the opposite ends of the outer face.

5. An assembly for use in making a measurement of a blood parameter comprising:
   an optical head including a body having an outer face, means for directing light from said outer face of the body and means for receiving light through the outer face of the body;
   a cuvette including a housing having a passage therein, said passage having a biocompatible surface and being adapted to receive blood;
   said housing having a wall with an outer face;
   said cuvette including an optical window leading from said outer face of the housing to said passage, said optical window being transmissive to an optical signal from the optical head and an optical signal from the passage so that the parameter of the blood can be measured;
   the optical window including a region of the wall and a deformable optical coupling element on said outer face of the housing at said region of said wall;
   a pivotal connection for pivoting the cuvette to the optical head for pivotal movement to a closed position in which said outer faces are in confronting relationship; and
   a retainer for retaining the cuvette and the optical head in the closed position.

6. A cuvette for use in making a measurement of a blood parameter, said cuvette comprising:
   a housing having a passage therein, said passage having a biocompatible surface and being adapted to receive blood;

said housing having a wall with an outer face;

an optical window leading from said outer face to said passage, said optical window being transmissive to an optical signal so that the parameter of the blood can be measured;

a magnet carried by said wall for use in providing information about the cuvette;

said passage being elongated and the magnet and the optical window being spaced longitudinally of the passage; and the optical window being bisected by an axial reference lane which extends through a longitudinal axis of the passage and said magnet lying on one side of said plane.

7. A cuvette as defined in claim 6 wherein the optical window includes a region of the wall and a deformable optical coupling element on said outer face at said region of said wall.

8. A cuvette as defined in claim 6 including means on said housing for use in releasably coupling the housing to an optical head.

9. A cuvette as defined in claim 6 wherein said outer face is generally flat.

10. A cuvette as defined in claim 6 wherein said outer face is generally flat and elongated, the cuvette includes first and second coupling members adjacent the opposite ends of the outer face, said optical window and said magnet are between the first and second coupling members.

11. A cuvette as defined in claim 10 wherein the first coupling member is useful in pivoting the cuvette to an optical head and the optical window includes a deformable optical coupling element on said outer face between the first coupling member and the magnet.

12. A cuvette as defined in claim 6 wherein said magnet is the only magnet carried by said housing.

13. A cuvette for use in making a measurement of a blood parameter, said cuvette comprising:

a housing having a passage therein, said passage having a biocompatible surface and being adapted to receive blood;

said housing having a wall with an outer face;

an optical window leading from said outer face to said passage, said optical window being transmissive to an optical signal so that the parameter of the blood can be measured;

a magnet carried by said wall for use in providing information about the cuvette;

said passage being elongated and the magnet and the optical window being spaced longitudinally of the passage; and said wall having a recess opening at said outer face and said magnet being retained in said recess.

14. A cuvette as defined in claim 13 wherein said recess is a first recess and said wall has a second recess adjacent the first recess which is sized to receive said magnet.

15. A cuvette as defined in claim 14 wherein the passage extends completely through the housing and is sterile, the magnet and the optical window are oriented so that an axial reference plane extending through a longitudinal axis of the passage bisects the optical window and said magnet and said first and second recesses are on one side of said plane.

16. A cuvette as defined in claim 13 wherein the optical window includes a deformable optical coupling element and the magnet is spaced from the deformable optical coupling element.

17. A cuvette as defined in claim 13 wherein the optical window includes a region of said wall and said region is thinner than an adjacent portion of said wall.

* * * * *

UNITED STATES PATENT AND TRADEMARK OFFICE
CERTIFICATE OF CORRECTION

PATENT NO. : 5,289,255
DATED : February 22, 1994
INVENTOR(S) : Mullin et al It is certified that error appears in the above-identified patent and that said Letters Patent is hereby corrected as shown below:

Column 4, line 12 after "assembly" insert -- 11 --.

Column 8, line 26 after "coupling" insert -- the housing --.

Signed and Sealed this

Nineteenth Day of July, 1994

Attest:

BRUCE LEHMAN

*Attesting Officer*     Commissioner of Patents and Trademarks